US009269278B1

(12) United States Patent
Turner (10) Patent No.: US 9,269,278 B1
(45) Date of Patent: Feb. 23, 2016

(54) METHODS AND SYSTEMS FOR DETERMINING RISK OF INJURY AND ATHLETIC PERFORMANCE TRAINING AND TREATMENT PROGRAMS

(71) Applicant: Mark Allan Turner, Naperville, IL (US)

(72) Inventor: Mark Allan Turner, Naperville, IL (US)

( * ) Notice: Subject to any disclaimer, the term of this patent is extended or adjusted under 35 U.S.C. 154(b) by 210 days.

(21) Appl. No.: 14/152,076

(22) Filed: Jan. 10, 2014

(51) Int. Cl.
*A63B 69/00* (2006.01)
*G09B 9/00* (2006.01)
*G09B 19/00* (2006.01)

(52) U.S. Cl.
CPC ..................................... *G09B 19/00* (2013.01)

(58) Field of Classification Search
USPC ....................................................... 434/247
See application file for complete search history.

(56) References Cited

U.S. PATENT DOCUMENTS

| 8,968,156 B2* | 3/2015 | Ellis ..................... A61B 5/1038 434/247 |
| 2013/0236867 A1* | 9/2013 | Avni .................... G09B 19/003 434/247 |

* cited by examiner

*Primary Examiner* — Kesha Frisby
(74) *Attorney, Agent, or Firm* — Patula & Associates, P.C.

(57) ABSTRACT

The present subject matter relates to methods and systems for assessing an athlete's risk of injury and for determining athletic performance training and treatment programs. The methods and systems comprise a series of observational and objective medical tests, recorded electronically through a customized software and mobile application package, which allows for pre-diagnosis of or propensity for potential injury. Test results are collected, analyzed and then used to recommend both treatment and performance training recommendations for the purposes of safety and athletic performance enhancement.

16 Claims, 6 Drawing Sheets

FINAL REPORT (EXAMPLE)

Observations

Risk:  LOW   MED   HIGH

(Example) - Michael Smith / 2015 QB is at:                                    (High Risk – Shoulder)

Analysis - Key Points:

1. Hip hinging

Hip hinging is a necessary movement mechanic for all athletes for many sports movements such as jumping, decelerating and quickly changing directions. When an athlete is unable to properly rotate through their hips, they will instead rotate through the low back, which in turn could lead to low back pain. In order to address faulty hip hinging mechanics, it is important to practice it as well as strengthen the hamstrings and glutes to help learn how to sit back better.

2. Valgus knee position through movements:

A valgus knee position is anytime an athlete's knees adduct (fall in) through a movement. This depicts an energy leak, leading to increased stress being placed on their knees. To address this issue, it is important to focus technically on pushing the knees out as well as strengthening the glute muscles.

3. Lateral pelvic shift to right on Squat and landing of Box Jump:

Occurs when an athlete shifts to one side or the other at bottom of the their Squat and/or landing of the Box Jump. It is important to note most athletes will have some sort of shift to one side or the other, but ideally speaking one wants this shift to be as minimal as possible. The reasons for placing more weight on onside than the other can vary from past injury, weakness or movement mechanics. When an athlete has a significant shift in weight, it requires one side of the body to control more shear forces from that particular movements, which could lead to an injury. It is important to recognize this type of error and address it through proper mechanics and strengthening of the hips.

4. Deceleration capabilities

Deceleration is one of the most important things an athlete can learn; it is everywhere in sports. It is the ability to stop one's moment in a controlled manner and in most instances transition to another movement. For most athletes, you will see them continue to move forward, allow the knees to fall in or various other errors. With such errors, the athlete is exposed to a greater stress being placed on the body, which can lead to potential injury. It is important with this need to work technically on stopping in a controlled manner.

5. Shoulder Abduction

From the muscle testing, it was found that his right shoulder abduction is 19% weaker than his left arm. This means his rear deltoids are not going to be able to help him decelerate when throwing, leading to a great potential for impingement. This could also lead to decreased throwing potential and shoulder fatigue as the season goes along.

FIGURE 6

METHODS AND SYSTEMS FOR DETERMINING RISK OF INJURY AND ATHLETIC PERFORMANCE TRAINING AND TREATMENT PROGRAMS

TECHNICAL FIELD

The exemplary teachings herein pertain to methods and systems for determining risk of injury and for determining specific athletic performance training and treatment programs to address that risk of injury, and in particular, to methods and systems which: analyze, grade and report a participant's level of risk of injury; conduct tests customized by gender and sport to determine where an injury is likely to occur; and determine appropriate training programs and/or treatment programs according to the test results.

BACKGROUND

There exist various methods and systems in the fitness and/or health industries to determine training plans or to determine treatment plans for injuries or illnesses. However, there are no known methods and systems which can be used to accurately assess the risk of injury to a particulate athlete for a specific sport, and to provide a customized fitness program to address that risk of injury and improve the particular athlete's performance for that specific sport. Unlike the present methods and systems disclosed herein, these known methods and systems are wholly inadequate and inapplicable for determining risk of injury and for determining specific athletic performance training and treatment programs to address that risk of injury.

For example, U.S. Patent Application Publication No. 2013/0138734 A1 published on May 30, 2013 to Crivello et al. discloses an interactive training method and system intended to develop peak user performance. The '734 system and method receives physical user data, medical history data and athletic goal data for the user, determines a baseline data set for the user, and generates a training routine for the user based on the baseline data set and the user data, including selecting a plurality of exercises for the user directed towards the athletic goal data. The '734 system and method differs significantly from the present methods and systems disclosed herein. Unlike the present method and system disclosed herein, the '734 system and method does not assess risk of injury for a particular athlete for a specific sport, and does not seek to improve athletic performance through customized athletic performance training and treatment programs/recommendations for the particular athlete for the specific sport, inter alia.

U.S. Pat. No. 8,388,530 B2 issued on Mar. 5, 2013 to Shusterman discloses a personalized monitoring and healthcare information management system using physiological basis functions, which provides a medical assessment specific to neurology concerns. The '530 method and system is intended to provide a serial-analysis based on the concept of personalized basis functions, which are monitored to detect an individual's changes associated with specific physiological activity or a sequence, transition or combination of activities, that can be used for information management, decision support, and diagnosis. The '530 system and method differs significantly from the present methods and systems disclosed herein. Unlike the present method and system disclosed herein, the '530 system and method does not assess risk of injury for a particular athlete for a specific sport, and does not seek to improve athletic performance through customized athletic performance training and treatment programs/recommendations for the particular athlete for the specific sport, inter alia.

U.S. Patent Application Publication No. 2012/0245973 A1 published on Sep. 27, 2012 to Pandya discloses methods for analyzing job functions and job candidates and for determining their co-suitability. The '973 system and method is used to conduct an elemental analysis of a job's functions and requirements, conduct a medical diagnosis of a worker to determine the physical capabilities and limitations of the worker, and compare the elemental analysis and the medical diagnosis to determine whether the worker can function in a particular job. The '973 system and method differs significantly from the present methods and systems disclosed herein. Unlike the present method and system disclosed herein, the '973 system and method does not assess risk of injury for a particular athlete for a specific sport, and does not seek to improve athletic performance through customized athletic performance training and treatment programs/recommendations for the particular athlete for the specific sport, inter alia.

U.S. Pat. No. 7,996,242 B2 issued on Aug. 9, 2011 to Fueyo et al. discloses a method and system for automatically developing neuropsychiatric treatment plans based on neuroimage data. The '242 method and system receives a set of diagnoses for a patient, analyzes medical information in a set of electronic medical literature sources for potential therapies associated with treatment of each identified condition in the set of diagnoses, identifies the potential therapies associated with the treatment of each diagnosed condition, selects a set of recommended therapies from the potential therapies based on portions of the medical literature describing each therapy in the potential therapies and a medical history for the patient, and generates a treatment plan comprising the set of recommended therapies to treat each diagnosed condition in the set of diagnoses. The '242 system and method differs significantly from the present methods and systems disclosed herein. Unlike the present method and system disclosed herein, the '242 system and method does not assess risk of injury for a particular athlete for a specific sport, and does not seek to improve athletic performance through customized athletic performance training and treatment programs/recommendations for the particular athlete for the specific sport, inter alia.

U.S. Pat. No. 7,615,342 B2 issued on Nov. 10, 2009 to North discloses an ACTN3 genotype screen for athletic performance. The '342 method and system is intended to select or match a sport or sporting event to an individual, predict athletic performance, and design training regimens by assessing ACTN3 genotype along with other known fitness-related genes and/or with physiological tests, physical measurements and/or psychological assessments. The '342 system and method differs significantly from the present methods and systems disclosed herein. Unlike the present method and system disclosed herein, the '342 system and method does not assess risk of injury for a particular athlete for a specific sport, and does not seek to improve athletic performance through customized athletic performance training and treatment programs/recommendations for the particular athlete for the specific sport, inter alia.

U.S. Patent Application Publication No. 2009/0070144 A1 published on Mar. 12, 2009 to Haider discloses a method and system for stroke prevention and care. The '144 system and method is intended to evaluate patient risk factors and manage the care of patients with risk factors for neurological syndromes. A form-based data entry device is used to retrieve medical history data of a patient, to enter updated data, and to request further medical tests and studies. A rule-based analysis engine is used to process the data so as to permit a user to interact with the system so as to determine a suitable care path for either long-term or acute situations. The '144 system and method differs significantly from the present methods and systems disclosed herein. Unlike the present method and system disclosed herein, the '144 system and method does not assess risk of injury for a particular athlete for a specific sport, and does not seek to improve athletic performance through customized athletic performance training and treatment programs/recommendations for the particular athlete for the specific sport, inter alia.

U.S. Pat. No. 7,264,554 B2 issued on Sep. 4, 2007 to Bentley discloses a method and system for analyzing and improving the performance of an athletic motion such as a golf swing. The '554 method and system requires instrumenting a user with inertial sensors and video cameras; monitoring a golf swing or such other athletic motion of interest; using a library of performance data for analysis of the test results to yield a single, kinetic index score for the motion; and prescribing a user-specific training regime with exercises selected from a library of standardized exercises using standardized tools and training aids. The '554 system and method differs significantly from the present methods and systems disclosed herein. Unlike the present method and system disclosed herein, the '554 system and method does not assess risk of injury for a particular athlete for a specific sport, and does not seek to improve athletic performance through customized athletic performance training and treatment programs/recommendations for the particular athlete for the specific sport, inter alia.

U.S. Patent Application Publication No. 2005/0273359 A1 published on Dec. 8, 2005 to Young discloses a system and method of evaluating preoperative medical care and determining recommended tests based on patient health history and medical condition and nature of surgical procedure. The '359 system and method obtains patient health history through patient response questionnaires, and analyzes data to determine recommended preoperative medical testing. Evaluation tables of surgical procedures and corresponding preoperative medical tests are generated, and recommended preoperative medical testing as indicated from the evaluation tables is scheduled. The '359 system and method differs significantly from the present methods and systems disclosed herein. Unlike the present method and system disclosed herein, the '359 system and method does not assess risk of injury for a particular athlete for a specific sport, and does not seek to improve athletic performance through customized athletic performance training and treatment programs/recommendations for the particular athlete for the specific sport, inter alia.

U.S. Patent Application Publication No. 2005/0015002 A1 published on Jan. 20, 2005 to Dixon et al. discloses an integrated protocol for diagnosis, treatment, and prevention of bone mass degradation such as osteoporosis. The '002 system and method integrates bone mass measurement techniques with various preventive and treatment measures to create a protocol for the prevention and treatment of the bone related condition. The system measures a bone characteristic level in the patient's bones to yield a score, conducts a gait analysis to yield a gait characterization, measures a bone mass marker concentration in the patient's body fluids to yield a bone marker level, and prescribes one or more therapies. The '002 system and method differs significantly from the present methods and systems disclosed herein. Unlike the present method and system disclosed herein, the '002 system and method does not assess risk of injury for a particular athlete for a specific sport, and does not seek to improve athletic performance through customized athletic performance training and treatment programs/recommendations for the particular athlete for the specific sport, inter alia.

As can be seen, these known prior art methods and systems fail to address issues related to the risk of athletic injury. They do not contemplate, nor could they be adequately used in assessing such risk of injury for a particular athlete for a specific sport. They do not seek to improve athletic performance through customized athletic performance training and treatment programs/recommendations for a particular athlete for a specific sport. The level of testing, analysis, result communication and follow-up necessary for meaningful assessment of risk of athletic injury is not considered in any of these applications.

These known prior art methods and systems lack the ability to conduct and analyze a series of observational assessments and computerized muscle testing regimens, to assess risk of injury of a particular athlete for a particular sport, and to develop customized training and/or treatment recommendations and other relevant information in the manner achieved by the present method and system disclosed herein.

Accordingly, to address the limitations and disadvantages of the above methods and systems, a method and system for determining risk of injury and for determining specific athletic performance training and treatment programs to address that risk of injury is needed. The methods and systems disclosed herein fulfill such needs. It is desired that the presently disclosed methods and systems for providing the above benefits be applicable to any instances or applications wherein the assessment of risk of physical injury is to be analyzed.

SUMMARY

The exemplary technique(s), system(s) and method(s) presented herein provide for a comprehensive analysis of the level of risk of injury of an athlete, customized both by sport and gender, through data assessment in association with computerized systems utilizing software and databases operating on appropriate physical hardware. The assessment tool of the disclosed methods and systems assigns a defined numerical value to each of the athlete's test results. The method and system analyzes the test results, and the results of the analysis are provided to the user in a report having training and/or treatment recommendations specific to that athlete, the athlete's sport and the athlete's level of risk of injury.

The assessment tool comprising a series of static observational assessments and a computerized muscle testing regimen which are scored and then used to assess the level of risk of athletic injury, and to recommend the appropriate training and/or treatment programs to address that risk. An athlete proceeds through one or more assigned testing stations which may include static assessment, scoliosis screening, gait analysis, orthopedic screening, breathing test, grip strength, overhead squat, single leg squat, box jump, single leg broad jump, push-up, double leg squat, other muscle tests and/or other medical or physical tests. Where applicable, the results of the muscle tests or other tests are captured and recorded electronically by suitable sensors, dynamometer or other muscle testing devices.

The results of these tests are assigned specific point values. Data from the tests is transmitted to a protected server, whereupon the system analyzes the data and the assigned point values, and then prescribes an overall risk assessment. Based on the analyzed data and the determined risk assessment, the method and system recommends one or more performance training programs and/or one or more treatment programs, which recommendations are provided to the athlete or the athlete's parent, coach, trainer, etc. The testing results can answer many serious questions or concerns that an athlete might have about future injury risk, such as where that injury is likely to occur, and what the athlete, coach, trainer and/or family can do to help address it.

Accordingly, it is an object of the methods and systems disclosed herein to provide assessments on risk of injury, and in particular, an athlete's level of risk of injury for a particular sport.

It is another object of the methods and systems disclosed herein to determine athletic performance training and treatment programs for an athlete for a particular sport based upon assessed risk of injury.

It is another object of the methods and systems disclosed herein to pre-diagnose potential season-ending or career-ending injuries to an athlete before they happen.

It is another object of the methods and systems disclosed herein to provide analytical tools to preform risk analysis based on a series of observational assessments and computerized muscle testing regimens.

Additional objects, advantages and novel features will be set forth in part in the description which follows, and in part will become apparent to those skilled in the art upon examination of the following and the accompanying drawings or may be learned by production or operation of the examples.

BRIEF DESCRIPTION OF THE DRAWINGS

The drawing figures depict one or more implementations in accord with the present teachings, by way of example only, not by way of limitation. In the drawing figures, like reference numerals refer to the same or similar elements.

DETAILED DESCRIPTION

The following description refers to numerous specific details which are set forth by way of examples to provide a thorough understanding of the relevant method(s) and system(s). It should be apparent to those skilled in the art that the present disclosure may be practiced without such details. In other instances, well known methods, procedures, components, hardware and circuitry have been described at a relatively high-level, without detail, in order to avoid unnecessarily obscuring aspects of the present disclosure. While the description refers by way of example to methods and systems for assessing the level of risk of injury to an athlete, it should be understood that the method(s) and system(s) described herein may be used in any situation where risk assessment testing is needed or desired.

As discussed in more detail below, the method and system disclosed herein comprises a dynamic tool that reflects the risk of injury for a particular athlete with respect to participation in a specific sport or activity. The method and system further generates a report which details, inter alia, specific or targeted treatment and training programs to address that risk of injury. The final report allows a user to understanding exactly how likely the athlete is to be injured, where that injury might occur, and exactly how to fix it. The proactive testing of the method and system reduces an athlete's overall risk of injury by as much as approximately 70% and helps reduce the risk of non-traumatic injury before it occurs. The method and system assists the user, who may be an athlete or an athlete's parent or coach, or other individual associated with the athlete, in reaching two main objectives, the safety of the athlete and the improved performance of the athlete, resulting in more successful competition. The understanding which the method and system provides regarding the athletic health of each athlete and having a proactive strategy to improve it, immediately provides a strategic advantage off the field and a performance advantage on the field.

Figure 1:
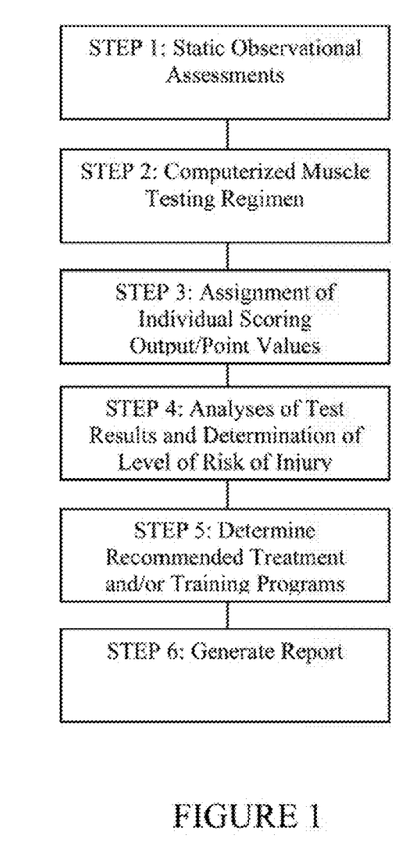
FIG. 1 is a flow chart of the overall method and system of the present disclosure.

FIG. 1 illustrates the overall steps of a preferred embodiment of the method and system with respect to the assessment of an athlete's risk of injury. Step 1 involves the capture of data related to static observational assessments, tests or measurements of the athlete, which data is entered into the system via any suitable computerized user interface and input device, and stored in a database or other suitable computerized data storage or memory device. Step 2 involves the capture of data related to a computerized muscle testing regime, which data is entered into the system via any suitable muscle testing equipment such as a Tracker Freedom® Wireless Muscle Testing system manufactured by JTech Medical of Salt Lake City, Utah, and stored in a database or other suitable computerized data storage or memory device. Step 3 involves the assignment of or generation of an individual scoring output or point values for each of the static observational assessments and the computerized muscle testing regimen. Step 4 involves the analysis of the results of the static observational assessments and the computerized muscle testing regimen, and the point values thereof, and the determination of the risk of injury for the athlete. Step 5 involves the determination of the recommended treatment and/or training programs for the athlete based on the analysis and determination of the risk of injury for the athlete. Finally, step 6 involves the generation of a report providing the user with information related to the analysis and determination of the risk of injury for the athlete, and to the determination of the recommended treatment and/or training programs for the athlete. Further details of each of these steps are provided below.

Figure 2:
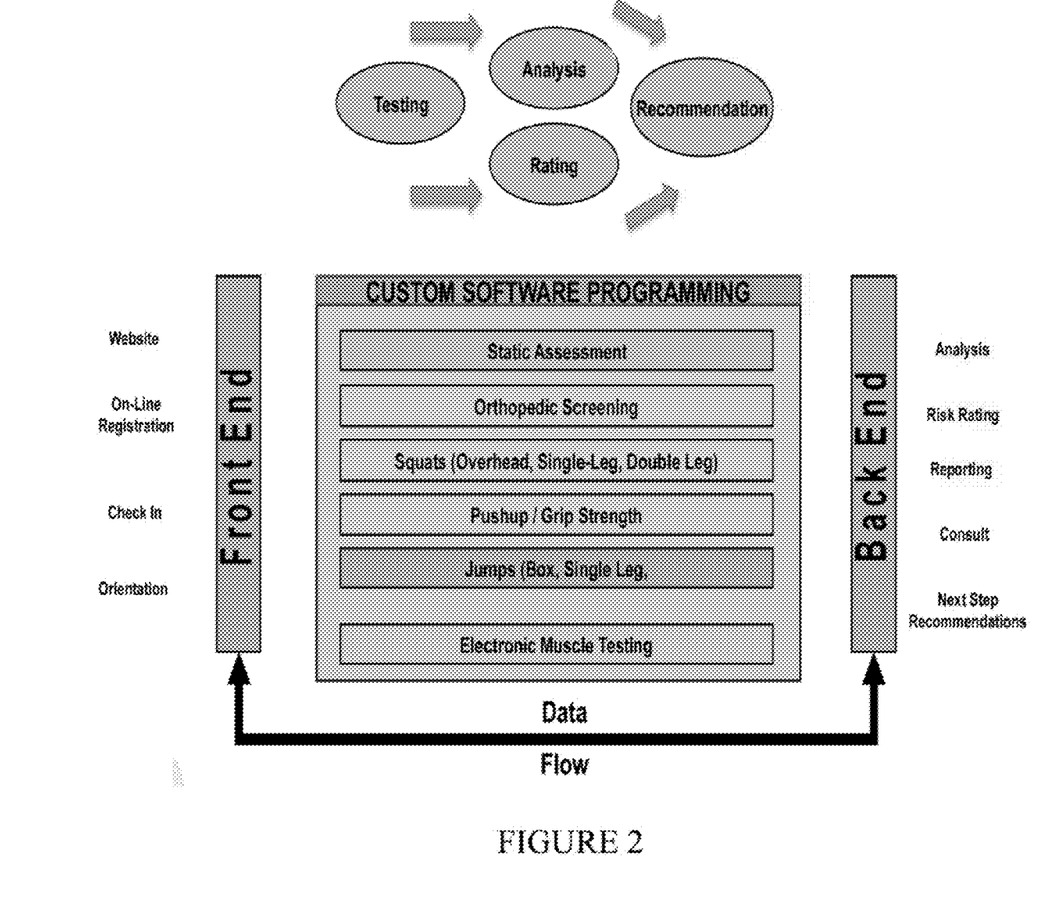
FIG. 2 is a schematic diagram of the overall method and system of the present disclosure.

As can be seen in the diagrams depicted in FIG. 2, the data flow in the method and system proceeds in general from testing, to analysis and rating, to recommendation. As further can be seen, this data flow runs from the front end of a computerized system, preferably comprising an on-line custom software program accessible via a website, to the back end of the computerized system providing the final report. The front end of the system preferably includes an on-line registration, check-in procedure and orientation for the athlete or user. The back end of the system preferably includes the analysis, risk rating, reporting, consultation and next step recommendations. The software programming includes the capture of data through static assessment, orthopedic screening, various physical tests such as squats including overhead, single-leg and/or double leg squats, pushups, grip strength, and jumps including box, single leg and/or double leg jumps, and electronic muscle testing.

Diagnostic testing begins with a series of static observational assessments, evaluating specific performance related movements, preferably captured on video and stored in the system. As a pre-checkup, the athlete will be observed when asked to perform certain stretches or exercises. By observing possible deficiencies, insights can be gained about what weaknesses to expect prior to the computerized muscle testing session. Appropriate data from the static observational assessments can be entered into the system in any suitable manner. The system then assigns or generates a point value for each of the assessments.

Figure 3:
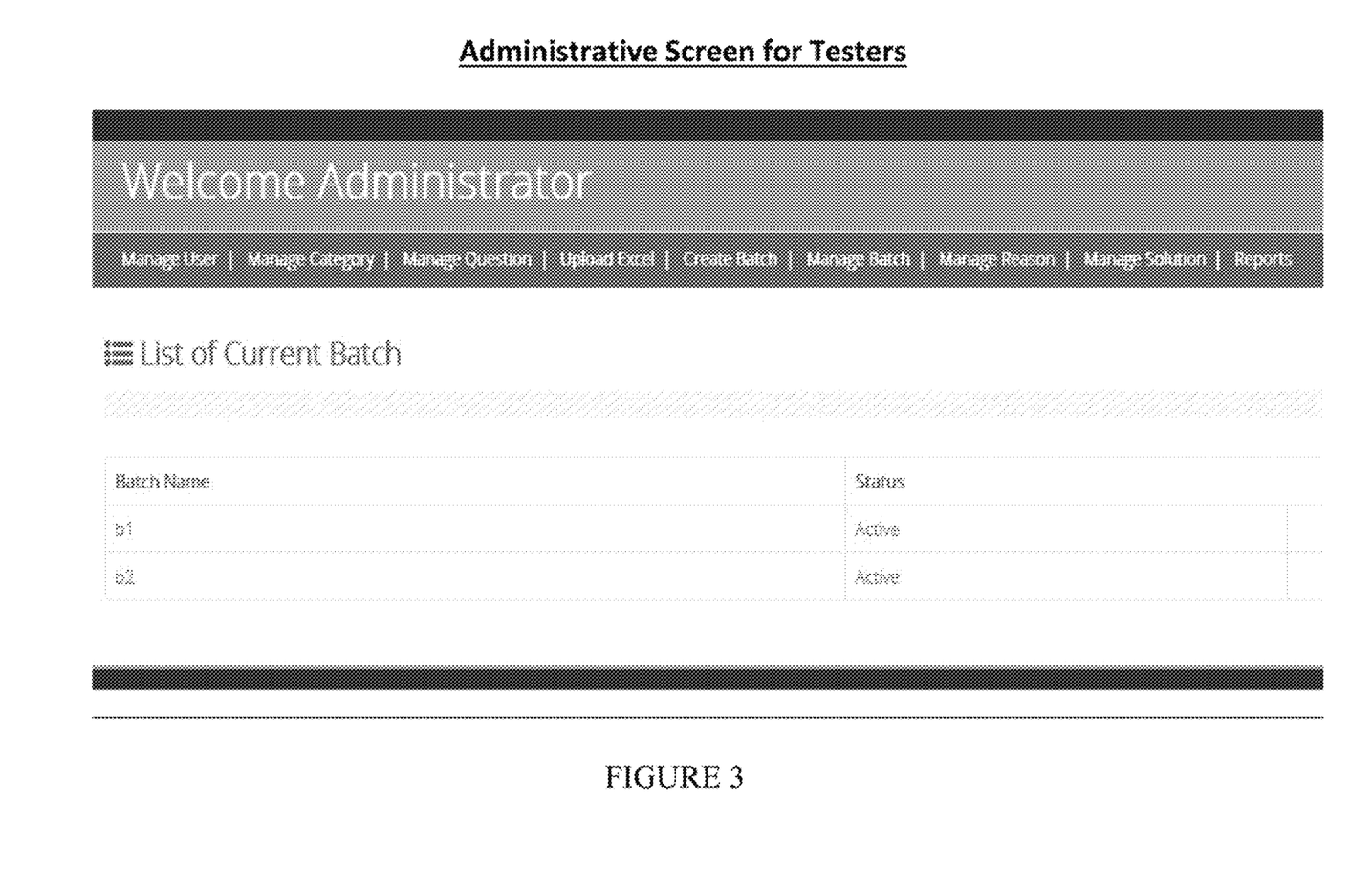
FIG. 3 is an exemplary administrative screen for testers of a preferred embodiment of the present disclosure.

FIG. 3 illustrates an exemplary administrative screen for testers where a user account can be established, test data captured for that use, and the analysis, reports and recommendations for that user can be generated, displayed and stored. A number of tabs which the tester or user can select to go to the corresponding screen or page, preferably include the following screen headings: manage user, manage category, manage question, upload excel, create batch, manage batch, manage reason, manage solution and reports. For example, FIG. 3 illustrates the screen when the tab for Manage Batch is selected.

Figure 4:
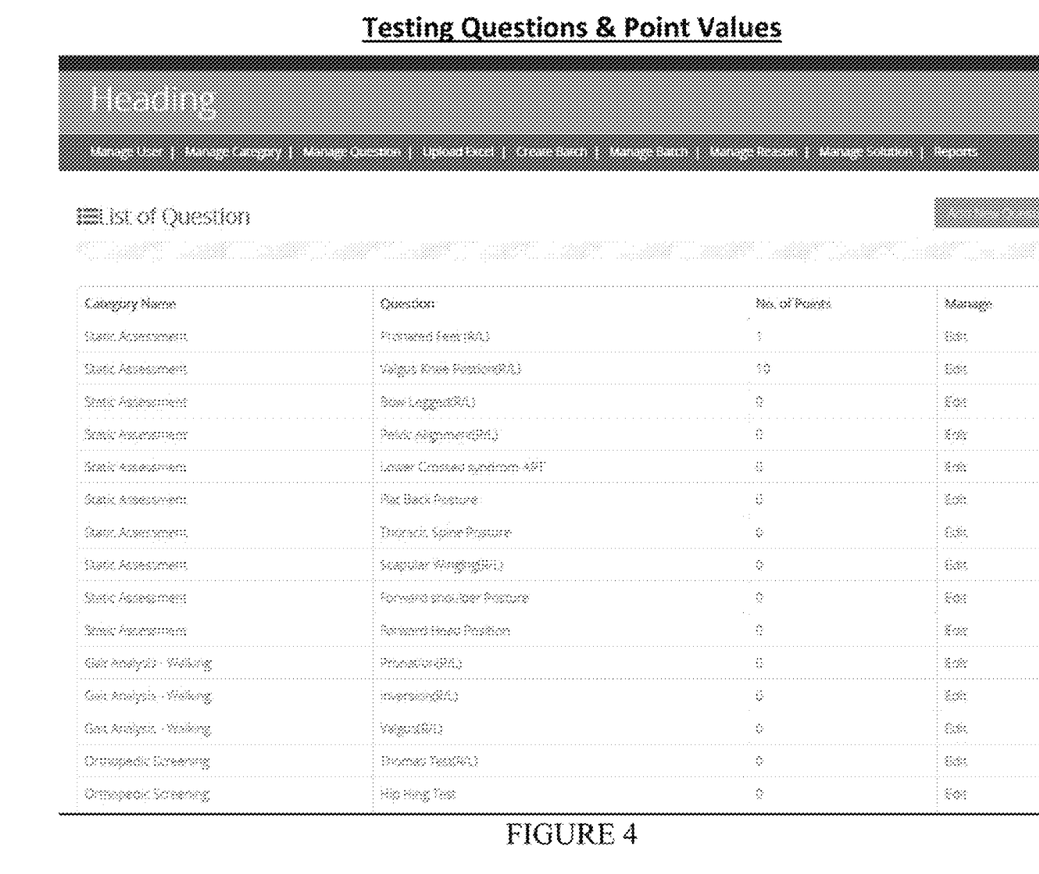
FIG. 4 is an exemplary testing questions and points values screen of a preferred embodiment of the present disclosure.

Similarly, FIG. 4 illustrates an exemplary testing questions and points values screen when the tab for Manage Questions is selected. The screen in FIG. 4 displays a list of questions corresponding a particular assessment or test. The point value associated with each assessment or question is provided, along with the option to manage or edit the assessment, question or point value. Each test question is given a pass/fail designation and assigned a specific point value, based on importance and overall health related impact for a particular sport or activity, or for an athlete's particular position played for a particular sport. Point values can be adjusted to more accurately evaluate a patient's likelihood for injury, as more data is gathered and evaluated. For any individual category failure, a training/treatment recommendation is made available in a drop down menu for the individual tester to select, that will show up on the final individual report.

For ease of illustration, not all of the assessments/questions are shown in FIG. 4. It should be understood that the tester or user of the system can scroll down for a complete list of assessments or tests. For example, the following testing categories and corresponding point values are preferably provided in the testing questions and point values screen.

Pronated Feet (1 Pt): Failure=excessive stress on medial chain, foot, knee and hip. Recommendation=stabilization exercises foot, knee, hip, i.e., bosu, posture mats/kin boards.

Supinated Feet (1 pt): Failure=excessive stress on lateral chain, foot, knee and hip. Recommendation=stabilization exercises foot, knee, hip, i.e., bosu, posture mats/kin boards.

Externally Rotated Feet (1 pt): Failure=shortened stress on external hip rotators decreasing internal hip Range Of Motion. Recommendation=functional stretches for external hip rotator including (walking leg cross) roller trigger points to external hip rotators.

Valgus Knee Position (1 pt): Failure=excessive stress on medial chain. Recommendation=stabilization exercise to foot, knee and hip, i.e., VMO strengthening/terminal extensions, bosu, posture mats/KIN boards.

Vargus Knee Position (1 pt): Failure=excessive stress on lateral chain. Recommendation=stabilization exercises to foot, knee and hip, i.e., closed chain lateral registered movement, glute medius strengthening, bosu, posture mats/KIN boards.

Pelvic Alignment (1 pt): Failure=asymmetrical stress to hip mobilizers, i.e., flexion, extension, abductor, adduction. Recommendation=mobilization and stabilization exercises to pelvis, i.e., unilateral closed chain movements including but not limited to 90 degree leg squats, hip abduction, hip adduction, reverse lunges without rear foot contact to ground, etc.

Flat Back Posture (1 pt): Failure=excessive stress on Lower Back musculature. Recommendation=strengthening exercises to erectors and glutes, i.e., squats, reverse lunges, glute HAM, reverse extension.

Thoracic Spine Posture (1 pt): Failure=excessive stress and decrease Range Of Motion to thoracic spine. Recommendation=strengthening and stabilization exercises including but not limited to scapular retractions/pectoral stretches, shoulder shrugs and neck retraction.

Scapular Winging (5 pt): Failure=subscapularis dysfunction. Recommendation=referral to medical professional to rule out cervical component and/or rotator cuff dysfunction.

Forward Shoulder Posture (1 pt): Failure=excessive stress on rear delts and rotator cuff decelerations. Recommendation=strengthening and stabilization exercises including but not limited to rear delts, depression retractions, scapular retractions, extension rotators of shoulder, mobilization to open shoulders and chest, i.e., pullovers, pectoral flips, etc.

Forward Head Position (1 pt): Failure=weakened neck flexors, or excessive stress neck extensors. Recommendation=strengthening of neck musculature and posterior chain including but not limited to scapular retractions, chin retractions, neck extensions (manual), neck flexions (manual hand under chin), neck rotations (manual hand under lateral chin).

Atrophy (5 pts): Failure=neurological dysfunction or musculoskeletal dysfunction to involved tissue. Recommendation=medical referral to identify source and cause and plan of action, i.e., MRI, needle EMG, strengthening protocol, etc.

Scoliosis Test (3 pts): Failure=diagnosed or undiagnosed curvature of spine. Recommendation=refer for medical evaluation (functional, static, degrees, progression, etc.).

Hip Hinging Test (1 pt): Failure=unable to maintain lordodic posture. Recommendation=strengthen and stabilize pelvis and Lower Back, exercises to include but not limited to glute, ham, back extensions/reverse lunges/overhead squat movements.

Thomas Test (1 pt): Failure=unable to flex and extend opposite HIP in acceptable range. Recommendation=strength and stabilize hip flexors and extensors including but not limited to one leg squats/reverse lunges, cable hip flexions, cable hamstring paw backs.

Knee Flexion Extension (5 pts): Failure=unable to flex knee in acceptable normal Range Of Motion. Recommendation=refer for medical evaluation for cause, i.e., meniscal damage, adhesions, inflammatory or non-inflammatory arthritis.

Ankle Sheer (5 pts): Failure=excessive Range Of Motion at tibia, talus and joint. Recommendation=refer for medical evaluation to rule out ligamentous injury through MRI; strength and stabilize foot, knee and hip on both sides, i.e., bosu, stability mats, KIN boards.

Shoulder Abduction (5 pts): Failure=humeral elevation upon abduction of shoulder. Recommendation=strength and stabilize rotator cuff decelerators; depression retraction exercise of shoulder, external rotations, scapula retractions and shrugs.

Obriens Test (5 pts): Failure: pain or weakness during test. Recommendation=referral for medical evaluation to rule out labral tear, or inflammatory process producing posture test.

Modified Cervical Test (5 pts): Failure=patient unable to resist shoulder abduction with cervical spine in maximal extension and rotation to tested side weakness.

Recommendation=medical evaluation to rule out thoracic outlet syndrome/foraminal encroachment/cervical disc lesion.

Lewin Gaenslens Test: Failure=unable to extend hip with symmetric force or range. Recommendation=evaluation of SI function, see computerized result for correlation; begin unilateral strengthening exercises, i.e., one leg reverse lung (back foot off the floor unsupported)

Hip Range Of Motion (5 pts): Failure: Range Of Motion excessive or restricted in acceptable range (painful or painless). Recommendation=refer for medical evaluation of joint function; rule out labral tear, CAM impingement, leg calf perthes.

Lachmans (10 pts): Failure=Excessive anterior translation of tibia, femur (sheering). Recommendation=refer for medical evaluation of joint function; rule out previous surgical repair/injury.

Central Stenosis (10 pts): Failure=patient unable to restrict hamstring eccentric force with lumbar spine in passive extension. Recommendation=refer to for medical evaluation; rule out disc herniation, spondylolisthesis, ligamentum flavum, hyoertrophy, mass, etc.

Lower Cross Syndrome (5 pts): Failure=patient unable to fire muscular components in accepted sequence when extending hip. Recommendation=strength exercises to retrain; glute erector firing sequence; may include Russian stim, butt walks, one leg hamstring squats rear leg un-supported off ground.

Shoulder Range Of Motion (5 pts): Failure=Range Of Motion excessive or restricted in acceptance range (painful or painless). Recommendation=refer for medical evaluation of joint function; rule out labral tear, rotator cuff dysfunction, muscle imbalance.

Achilles Compression (5 pts): Failure=painful test on distal Achilles compression (edematous or not). Recommendation=check hip extension strength on affected side/calf, strength and stretching (seated standing calf raises), hip evaluation for asymmetry and compensatory stress to foot extensors.

Grip Strength (2 pts): Failure=patient unable to hang with straight arms less than 30 seconds. Recommendation=if left or right hand slips first, evaluate cervical radicular component; hand and elbow pathology initially ruled out previous to hang.

Single Leg Broad Jump: Posture (2 pts), Knee instability right/left (2 pts), 10% difference (1 pt), 20% difference (2 pts), 30% difference (5 pts): Failure=Patient was unable to take off or land in correct posture (forward lean asymmetrical); Patient unable to take off or land without sheering/adducting or abducting knee. Recommendation=accelerators and decelerators in addition to hip stabilizers/gluteus medius/T.F.L.

Double Leg Squat: Pronated feet R/L (1 pt), Valgus knee R/L (1 pt), Knee sheering (1 pt), Lateral pelvic shift (1 pt), Forward at bottom of squat: (1 pt).

Single Leg Squat: Pronated feet R/L (1 pt), Valgus knee R/L (1 pt), Knee sheering (1 pt).

Box Jump: Valgus knee R/L (1 pt), Knee sheering (1 pt), Forward upper body angle (1 pt), Loading shift R/L (1 pt).

Push Up: Scapular winging R/L (1 pt), Delayed lower torso (1 pt), Asymmetries in loading R/L (1 pt).

After the static assessment, the diagnosis process continues with a series of computerized muscle tests with medical evaluations and therapeutic observations designed to identify and assess risk factors for potential injury. The computerized muscle testing regimen measures the amount of force in pounds provided by the certain muscle. The computerized muscle testing software records the muscle testing result in the system. The system then assigns or generates a point value for each of the assessments. The computerized muscle testing is extremely accurate, and can serve as a confirmation to the pre-checkup phase.

Figure 5:
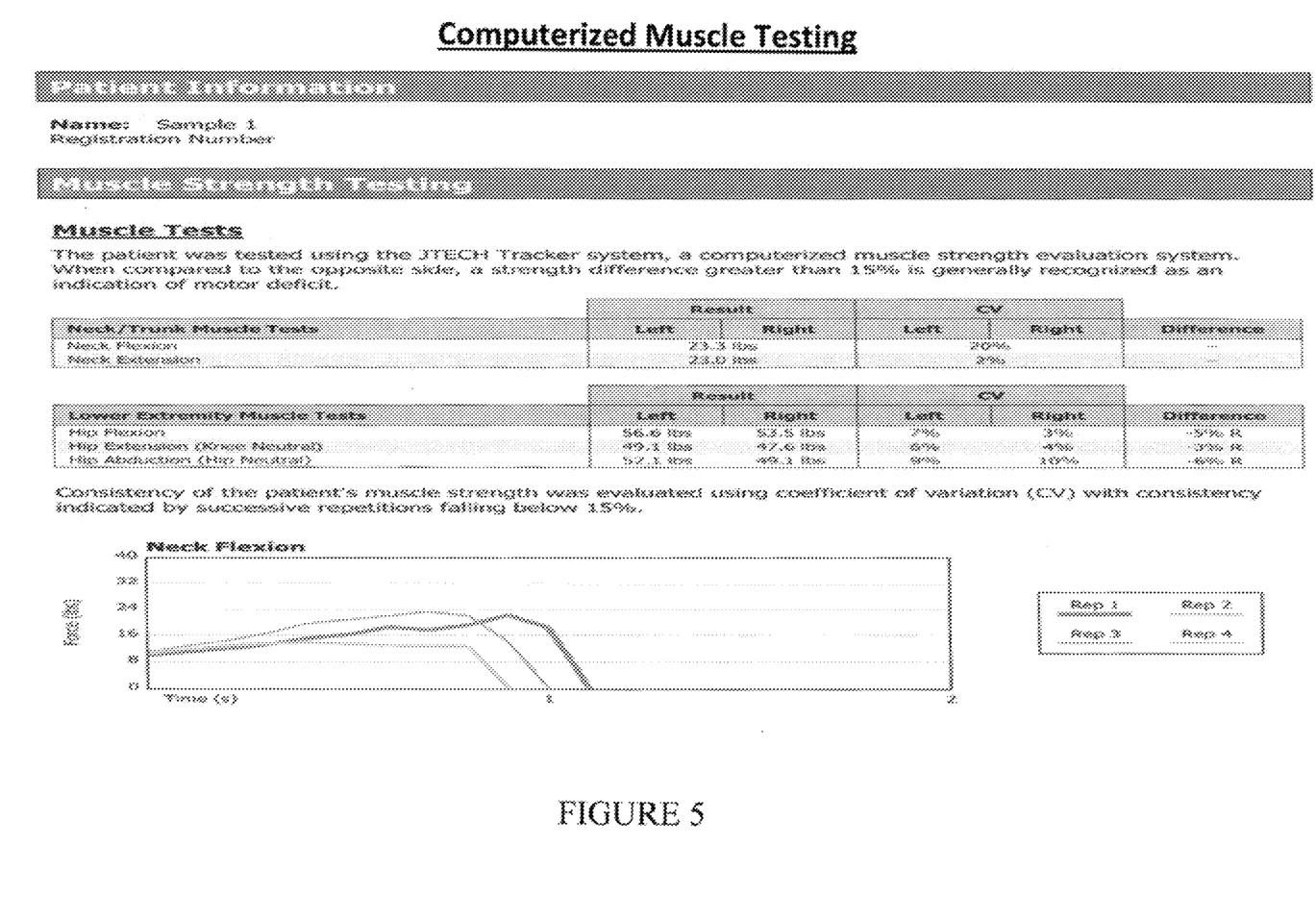
FIG. 5 is an exemplary chart illustrating the results of a computerized muscle test of a preferred embodiment of the present disclosure.

FIG. 5 illustrates an exemplary chart of a sample muscle test result. As can be seen the test results show in table form the force in pounds of a certain muscle, including left and right where appropriate. The test also measures the coefficient of variation, and the percent difference between left and right muscles where appropriate. A graph of the test results showing force in pounds over time is illustrated for a number of repetitions.

The point values assigned or generated by the system according to the muscle test results are, for example, as follows: 8-15% Deficit in symmetry (5 pts); 16-24% Deficit in symmetry (10 pts); 24% and greater Deficit in symmetry (15 pts); 8-15% Ratio Imbalance (5 pts); 16-24% Ratio Imbalance (10 pts); and 24% Ratio Imbalance (15 pts).

Patients are then provided with a risk assessment based off the results. In the risk assessment, there are preferably three ratings the patient can receive. There can be a low risk of injury, a moderate risk of injury and a high risk of injury. Thus, for example, an overall patient score of 0-6 pts would receive a low risk. An overall patient score of 7-15 pts would receive a moderate risk. An overall patient score of 16+ pts would receive a high risk. It should be understood that other scales could be used and are contemplated, such as a risk of injury on a scale of 1-10, etc.

If the patient receives a moderate to high risk of injury in a specific area, the method and system will give the athlete a training program in order to strengthen that certain weakness. By doing this, the assessment gives athletes a pathway to greater performance in their sport.

Once the risk assessment is given to the patient, the patient is expected to work on the areas in which he or she needs improvement. Provided that the patient does so, a follow-up computerized muscle test is conducted at a future date, for example four to five months later, to see whether there has been an advance in the previous weakness.

All point values for each test are preferably stored in a database, such that upon completion of each test and recordation of the test result, the system can automatically access the points database to determine and assign the appropriate point value to the entered test result. Similarly, the treatment and training recommendations are also preferably stored in another database, such that treatment and training recommendations can be automatically generated and displayed based upon the test results, both for individual assessments or tests, and for the overall assessment.

Further, the various tests, point values and treatment and training recommendations can be specific to a sport (e.g., baseball, football, swimming, volleyball, etc.), a specific position for the sport (e.g., pitcher, catcher, first baseman, or quarterback, running back, linebacker, etc.), and gender of the athlete (male or female). Different database subsets can be stored within the databases, and the system can access the appropriate subset based upon the athlete's gender, sport and position. For example, if a male football player who plays quarterback is being evaluated for risk of injury, the system can apply the specific subset of tests, point values, and treatment and training recommendations applicable to a male football quarterback. The one or more of the tests, point values and treatment and training recommendations can differ between the subsets for different athletes, sports and/or positions. Accordingly, subset testing in each category may also vary by sport, as will pass/fail diagnosis. For example, a failed shoulder flexion test may be considered high risk for injury for a gymnast, but a low risk for a football player.

Figure 6:
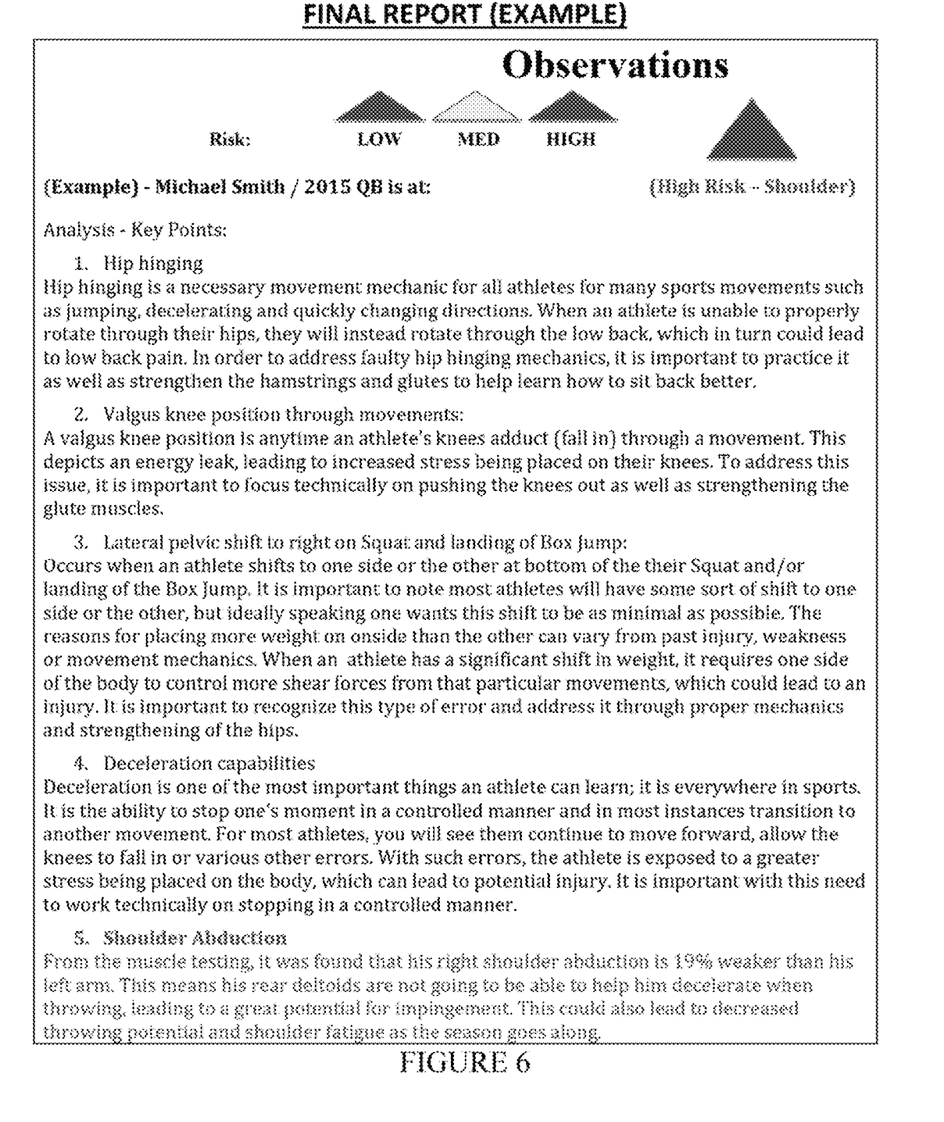
FIG. 6 is an exemplary final report of a preferred embodiment of the present disclosure.

FIG. 6 illustrates an exemplary final report generated by the system. In a report, the level of risk of injury can be identified as low, medium or high, and is preferably color coordinated as a green, yellow and red triangle or other indicia, respectively. The report can also indicate in what location the athlete is likely to be injured. In this example, a male football quarterback tested high risk for a right shoulder injury. An analysis of key points is provided as illustrated in the example report of FIG. 5. The report can also include information regarding the test results, including the information illustrated in FIGS. 4 and 5.

The components of the system can take any suitable form, including any suitable hardware, software or other computerized components including but not limited to servers, processors, databases, memory devices, mobile applications, etc., capable of adequately performing their respective intended functions, as may be known in the art. Further, while the embodiment(s) are illustrative of the structure, function and operation of the exemplary method(s) and system(s), it should be understood that various modifications may be made thereto with departing from the teachings herein.

While the foregoing discussion presents the teachings in an exemplary fashion with respect to the disclosed methods and systems for assessing risk of athletic injury, it will be apparent to those skilled in the art that the present disclosure may apply to any type of method and system for assessing risk. In general, the preferred methodology by category will comprise static, orthopedic, functional movement, strength and computerized testing. The subset of tests in these particular categories may be modified to address the assessment of any specific risk, person, sport or activity and/or position. For example, a static and functional component may be instituted into the method and system for head injury and concussion testing. The method and system can then evaluate a person's baseline and demonstrate a neurologic return to an accepted state of normal.

Further, while the foregoing has described what are considered to be the best mode and/or other examples, it is understood that various modifications may be made therein and that the subject matter disclosed herein may be implemented in various forms and examples, and that the method(s) and system(s) may be applied in numerous applications, only some of which have been described herein.

What is claimed is:

1. A system for assessing risk of injury, comprising:
   a computer software program operating on computer hardware including at least one processor;
   a user interface for inputting test results from static observational assessments into the computer program;
   a muscle testing device for conducting muscle tests and transmitting muscle test result data to the computer program;
   a database for storing point values for each static observational assessments test and each muscle test; and
   a database for storing training and treatment recommendations for each static observational assessments test and each muscle test;
   wherein the software program assigns a point value to the static observational assessments test results and the muscle test result data; and determines a predicted level of risk of injury.

2. The system of claim 1, wherein the system generate a report on the predicted level of risk of injury.

3. The system of claim 2, wherein the database for storing point values includes subsets according to a specific sport.

4. The system of claim 2, wherein the database for storing point values includes subsets according to a specific position for a specific sport.

5. The system of claim 2, wherein the database for storing point values includes subsets according to a specific gender of athlete.

6. The system of claim 2, wherein the database for storing training and treatment recommendations includes subsets according to a specific sport.

7. The system of claim 2, wherein the database for storing training and treatment recommendations includes subsets according to a specific position for a specific sport.

8. The system of claim 2, wherein the database for storing training and treatment recommendations includes subsets according to a specific gender of athlete.

9. A method for assessing risk of injury, comprising the steps of:
   performing a plurality of static observation assessments;
   performing a plurality of muscle tests;
   recording the test results of each of the plurality of static observation assessments and the plurality of muscle tests in a computer software program operating on computer hardware including at least one processor;
   assigning a point value from a database of point values to each of the test results;
   determining a level of risk of injury based upon the assigned point values.

10. The method of claim 9, further comprising the step of determining treatment and training recommendations from a database of treatment and training recommendations based upon the level of risk of injury.

11. The method of claim 10, wherein the database of point values includes subsets according to a specific sport.

12. The method of claim 10, wherein the database of point values includes subsets according to a specific position for a specific sport.

13. The method of claim 10, wherein the database of point values includes subsets according to a specific gender of athlete.

14. The method of claim 10, wherein the database of training and treatment recommendations includes subsets according to a specific sport.

15. The method of claim 10, wherein the database of training and treatment recommendations includes subsets according to a specific position for a specific sport.

16. The method of claim 10, wherein the database of training and treatment recommendations includes subsets according to a specific gender of athlete.

* * * * *